US008475641B2

(12) United States Patent
Marziali et al.

(10) Patent No.: US 8,475,641 B2
(45) Date of Patent: Jul. 2, 2013

(54) METHODS AND APPARATUS FOR PARTICLE INTRODUCTION AND RECOVERY

(75) Inventors: Andrea Marziali, North Vancouver (CA); David John Broemeling, Vancouver (CA); Dylan Corey Gunn, Vancouver (CA); Peter Jason Eugster, Vancouver (CA); Joel Pel, Vancouver (CA)

(73) Assignee: The University of British Columbia, Vancouver (CA)

( * ) Notice: Subject to any disclaimer, the term of this patent is extended or adjusted under 35 U.S.C. 154(b) by 239 days.

(21) Appl. No.: 12/865,384

(22) PCT Filed: Jan. 30, 2009

(86) PCT No.: PCT/CA2009/000111
§ 371 (c)(1),
(2), (4) Date: Jul. 29, 2010

(87) PCT Pub. No.: WO2009/094772
PCT Pub. Date: Aug. 6, 2009

(65) Prior Publication Data
US 2011/0048950 A1 Mar. 3, 2011

Related U.S. Application Data

(60) Provisional application No. 61/006,838, filed on Feb. 1, 2008, provisional application No. 61/006,837, filed on Feb. 1, 2008.

(51) Int. Cl.
*G01N 27/447* (2006.01)

(52) U.S. Cl.
USPC ........... 204/458; 204/457; 204/462; 204/608; 204/609; 204/613

(58) Field of Classification Search
USPC .................. 204/457, 458, 462, 608, 609, 613
See application file for complete search history.

(56) References Cited

U.S. PATENT DOCUMENTS

| 4,390,403 A | 6/1983 | Batchelder |
| 4,732,656 A | 3/1988 | Hurd |

(Continued)

FOREIGN PATENT DOCUMENTS

| CA | 2552262 A1 | 8/2005 |
| CA | 2523089 A1 | 4/2006 |

(Continued)

OTHER PUBLICATIONS

Asbury, Charles L. and Ger van den Engh, "Trapping of DNA in nonuniform oscillating electric fields", Biophysical Journal, 1998, 74:1024-1030.

(Continued)

*Primary Examiner* — Keith Hendricks
*Assistant Examiner* — Kourtney S Carlson
(74) *Attorney, Agent, or Firm* — Thomas C. Meyers; Brown Rudnick LLP (57) ABSTRACT

Particles may be injected into a matrix for concentration by scodaphoresis using a quadrupole injection field. Particles may be injected from two or more sample chambers simultaneously. Particle injection may be performed simultaneously with performing scodaphoresis. In some embodiments the particles are concentrated into a well containing fluid. The well can extend out of a plane of the matrix. Altering the relative phases of components of a scodaphoresis field permits concentration of selected particles and exclusion of other particles. Scodaphoresis methods may be applied to DNA, other bio-molecules and other particles.

23 Claims, 9 Drawing Sheets

U.S. PATENT DOCUMENTS

| | | | |
|---|---|---|---|
| 4,911,817 | A | 3/1990 | Kindlmann |
| 5,185,071 | A | 2/1993 | Serwer |
| 5,286,434 | A | 2/1994 | Slater et al. |
| 5,384,022 | A | 1/1995 | Rajasekaran |
| 5,609,743 | A | 3/1997 | Sasagawa |
| 5,938,904 | A | 8/1999 | Bader |
| 6,036,831 | A | 3/2000 | Bishop |
| 6,146,511 | A | 11/2000 | Slater |
| 6,193,866 | B1 | 2/2001 | Bader |
| 6,693,620 | B1 | 2/2004 | Herb |
| 6,824,664 | B1 | 11/2004 | Austin |
| 6,827,830 | B1 | 12/2004 | Slater et al. |
| 6,893,546 | B2 | 5/2005 | Jullien |
| 7,198,702 | B1 | 4/2007 | Washizu |
| 7,371,533 | B2 | 5/2008 | Slater et al. |
| 7,427,343 | B2 | 9/2008 | Han |
| 2001/0045359 | A1 | 11/2001 | Cheng |
| 2002/0036139 | A1 | 3/2002 | Becker |
| 2002/0081280 | A1 | 6/2002 | Curiel |
| 2002/0119448 | A1 | 8/2002 | Sorge |
| 2002/0179445 | A1 | 12/2002 | Alajoki |
| 2003/0027178 | A1 | 2/2003 | Vasmatzis |
| 2003/0215855 | A1 | 11/2003 | Dubrow |
| 2005/0164402 | A1 | 7/2005 | Belisle |
| 2005/0247563 | A1 | 11/2005 | Shuber |
| 2005/0247564 | A1 | 11/2005 | Volkel et al. |
| 2007/0215472 | A1 | 9/2007 | Slater et al. |
| 2007/0218494 | A1 | 9/2007 | Slater et al. |
| 2009/0120795 | A1 | 5/2009 | Marziali |
| 2009/0139867 | A1 | 6/2009 | Marziali |
| 2011/0048950 | A1 | 3/2011 | Marziali |
| 2011/0272282 | A1 | 11/2011 | Marziali |

FOREIGN PATENT DOCUMENTS

| | | | |
|---|---|---|---|
| CA | 2496294 | A1 | 8/2006 |
| CA | 2641326 | A1 | 8/2006 |
| JP | 2000-505545 | A | 5/2000 |
| JP | 2001-165906 | A | 6/2001 |
| JP | 2002-502020 | A | 1/2002 |
| JP | 2003-062401 | A | 3/2003 |
| JP | 2003-066004 | A | 3/2003 |
| JP | 2003-513240 | A | 4/2003 |
| JP | 2003-215099 | A | 7/2003 |
| JP | 2003-247980 | A | 9/2003 |
| WO | 9514923 | A1 | 6/1995 |
| WO | 9727933 | A1 | 8/1997 |
| WO | 9938874 | A2 | 8/1999 |
| WO | 0131325 | A1 | 5/2001 |
| WO | 0242500 | A2 | 5/2002 |
| WO | 03019172 | A2 | 3/2003 |
| WO | 2005072854 | A1 | 8/2005 |
| WO | 2006063625 | A1 | 6/2006 |
| WO | 2006081691 | A1 | 8/2006 |
| WO | 2009094772 | A1 | 8/2009 |
| WO | 2010051649 | A1 | 5/2010 |
| WO | 2010121381 | A1 | 10/2010 |

OTHER PUBLICATIONS

Asbury, Charles L. and Ger van den Engh, "Trapping of DNA by dielectrophoresis", Electrophoresis, 2002, 23:2658-2666.

Astumian, R. Dean, et al., "Fluctuation driven ratchets: molecular motors", Physical Review Letters, 1994, 72 (11):1766-1769.

Bier, Martin, et al., "Biasing brownian motion in different directions in a d-state fluctuating potential and an application for the separation of small particles", Physical Review Letters, 1996, 76(22):4277-4280.

Carle, G.F., et al., "Electrophoretic separation of large DNA molecules by periodic inversion of the electric field", Science, 1986, 232(4746):65-68.

Chacron, Maurice J. and Gary W. Slater, "Particle trapping and self-focusing in temporally asymmetric ratchets with strong field gradients", Physical Review E, 1997, 56(3):3446-3450.

Chu, Gilbert, "Bag model for DNA migration during pulsed-field electrophoresis", Proc Natl Acad Sci, 1991, 88:11071-11075.

Frumin, L.L., et al., "Anomalous size dependence of the non linear mobility of DNA", Phys Chem Commun, 2000, 11 (3):61-63.

Frumin, L.L., et al., "Nonlinear focusing of DNA macromolecules", Physical Review E—Statistical, Nonlinear and Soft Matter Physics, 2001, 64(2):021902-1-5.

Griess, Gary A., et al., "Cyclic capillary electrophoresis", Electrophoresis, 2002, 23:2610-2617.

Kopecka, K., et al., "Capillary electrophoresis sequencing of small ssDNA molecules versus the Ogston regime: fitting data and interpreting parameters", Electrophoresis, 2004, 25(14):2177-2185.

Magnasco, Marcelo, O., "Forced thermal ratchets", Physical Review Letters, 1993, 71(10):1477-1481.

Pel, J., et al., "Nonlinear electrophoretic response yields a unique parameter for separation of biomolecules", PNAS, 2009, 106(35):14796-14801.

Pel, J., "A novel electrophoretic mechanism and separation parameter for selective nucleic acid concentration based on synchronous coefficient of drag alteration (SCODA)", (Ph.D. Thesis published in 2009), Vancouver: University of British Columbia, 2009.

Rousseau, J., et al., "Gel electrophoretic mobility of single-stranded DNA: The two reptation field-dependent factors", Electrophoresis, 2000, 21(8):1464-1470.

Slater, G.W., et al., "Recent developments in DNA electrophoretic separations", Electrophoresis, 1998, 19 (10):1525-1541.

Slater, G.W., et al., "Theory of DNA electrophoresis: a look at some current challenges", Electrophoresis, 2000, 21:3873-3887.

Slater, Gary W., et al., "The theory of DNA separation by capillary electrophoresis", Current Opinion in Biotechnology, 2003, 14:58-64.

Tessier, F., et al., "Strategies for the separation of polyelectrolytes based on non-linear dynamics and entropic ratchets in a simple microfluidic device", Applied Physics A, 2002, 75:285-291.

Turmel, C., et al., "Molecular detrapping and band narrowing with high frequency modulation of pulsed field electrophoresis", Nucleic Acids Res, 1990, 18(3):569-575.

Viovy, J.L., "Electrophoresis of DNA and other polyelectrolytes: Physical mechanisms", Reviews of Modern Physics, 2000, 72(3):813-872.

Office Action mailed Aug. 19, 2011 for U.S. Appl. No. 11/815,760, filed Feb. 7, 2006.

Office Action mailed Dec. 27, 2010 for U.S. Appl. No. 11/815,760, filed Feb. 7, 2006.

Marziali, A. et al., "Novel electrophoresis mechanism based on synchronous alternating drug perturbation", Electrophoresis 2005, 26, 82-89.

Broemeling, D. et al., "An Instrument for Automated Purification of Nucleic Acids from Contaminated Forensic Sample", JALA 2008, 13, 40-48.

METHODS AND APPARATUS FOR PARTICLE INTRODUCTION AND RECOVERY

CROSS-REFERENCE TO RELATED APPLICATIONS

This application is a 35 U.S.C. §371 National Phase Application of PCT/CA2009/000111, filed Jan. 30, 2009 which claims priority to U.S. patent application No. 61/006,837 filed on 1 Feb. 2008 and entitled IMPROVED SCODA EXTRACTION and to U.S. patent application No. 61/006,838 filed on 1 Feb. 2008 and entitled IMPROVED SCODA DEVICE AND METHODS under 35 U.S.C. §119, both of which are hereby incorporated by reference.

FIELD

This invention relates to handling molecules or other particles. Embodiments of the invention provide methods and apparatus for introducing particles into a medium in which the particles can be separated and/or concentrated and for removing particles from such a medium. The invention may be applied to advantage where scodaphoresis is performed when the particles are in the medium.

BACKGROUND

Scodaphoresis (or "SCODA") is an approach that may be applied for concentrating and/or separating particles. SCODA may be applied, for example to DNA, RNA and other molecules. SCODA is described in:

PCT application WO 2005/072854A1 entitled Scodaphoresis and methods and apparatus for moving and concentrating particles;

PCT application WO 2006/081691A1 entitled Apparatus and methods for concentrating and separating particles such as molecules; and

*Novel electrophoresis mechanism based on synchronous alternating drag perturbation*, Marziali, A.; Pel, J.; Bizotto, D.; Whitehead, L. A. Electrophoresis 2005, 26, 82-89.

D. Broemeling, J. Pel, D. Gunn, L. Mai, J. Thompson, H. Poon, A. Marziali, *An Instrument for Automated Purification of Nucleic Acids from Contaminated Forensic Sample* JALA, 2008, 13, 40-48 all of which are hereby incorporated herein by reference. SCODA can involve providing a time-varying driving field that applies forces to particles in some matrix and a time-varying mobility-altering field that affects the mobility of the particles in the matrix. The mobility-altering field is correlated with the driving field so as to provide a time-averaged net motion of the particles toward a focus area.

Some modes of SCODA apply electric fields to a medium in which particles respond to the electric fields in a non-linear manner. In such modes, suitably time-varying electric fields can cause certain types of particles to be focussed at locations within the medium. The following discussion of SCODA is intended as an illustrative example only. In many practical cases, the instantaneous velocity of a particle in a medium under the influence of an electric field is given by:

$$\vec{v} = \mu \vec{E} \quad (1)$$

where $\vec{v}$ is the velocity of the particle, $\vec{E}$ is the electric field and μ is the mobility of the particle given, at least approximately, by:

$$\mu = \mu_0 + kE \quad (2)$$

where, $\mu_0$ and k are constants. Particles with larger values for k tend to be focussed more strongly than particles with smaller values for k.

In some cases, SCODA is performed by providing an electrical field having a rotating component and a quadrupole perturbation. The rotating component may be specified, for example, by:

$$E_x = E \cos(\omega t) \quad (3)$$

and $$E_y = E \sin(\omega t) \quad (4)$$

where E is a magnitude of the electric field component that rotates at an angular frequency ω, and $E_x$ and $E_y$ are respectively x- and y-components of the rotating electrical field. The perturbing quadrupole component may be specified, for example, by:

$$dE_x = -dE_q x \cos(2\omega t) \quad (5)$$

and $$dE_y = dE_q y \cos(2\omega t) \quad (6)$$

where $dE_x$ and $dE_y$ are respectively x- and y-components of the perturbing electrical field, x and y are distances from an origin at the center of the quadrupole field pattern and $dE_q$ is the intensity coefficient of the perturbing quadrupole field. With this SCODA field, the average radial velocity of a particle toward a focus location can be shown to be given by:

$$\overline{\vec{v}_r} = \frac{kEdE_q}{4}\vec{r} \quad (7)$$

where E is the magnitude of an electric field component that rotates at an angular frequency ω, $E_q$ is a measure of the quadrupole component of the electric field that varies at an angular frequency of 2ω, and $\vec{r}$ is a vector pointing toward the focus location and having a magnitude equal to the distance of the particle from the focus location.

The size of a spot into which particles can be focussed depends upon k as well as the rate at which the particles can diffuse in the medium as follows:

$$\frac{1}{R} = \sqrt{\frac{k}{D}} \quad (8)$$

where R is a radius of the focussed spot and D is a diffusion coefficient.

There is a need for practical and cost efficient methods and apparatus for introducing particles into a medium. There is a particular need for such methods and apparatus that are compatible with performing scodaphoresis to concentrate and/or separate the particles in the medium.

SUMMARY OF THE INVENTION

This invention has a range of aspects which include, without limitation:

apparatus for performing SCODA comprising modified wells for collecting particles;

apparatus configured for injecting particles into a matrix using a quadrupole electric field;

apparatus for performing SCODA having multiple injection chambers;

apparatus configured to perform reverse phase SCODA;

SCODA apparatus configurable to alter a shape of an area into which particles are focussed by altering duty cycles of SCODA waveforms;

controllers for apparatus for performing reverse phase SCODA;

controllers for apparatus for injecting particles into a matrix using a quadrupole electric field; and controllers for SCODA apparatus configured to alter duty cycles of SCODA waveforms;

improved methods for performing SCODA.

These aspects are not exhaustive and are also not mutually inclusive. Methods and apparatus according to some embodiments may incorporate two or more of these aspects.

One aspect of the invention provides apparatus for collecting particles. The apparatus comprises a layer of a matrix material (which is a gel in some embodiments) a SCODA controller connected to apply a SCODA field to the matrix material and a well passing through the layer of matrix material in a focus zone. The SCODA field is operable to concentrate particles in the layer into the focus zone. The well extends out of the layer of the matrix material.

Another aspect of the invention provides a scodaphoresis method. The method comprises applying a scodaphoresis field to particles in a matrix. The scodaphoresis field causes time averaged motion of the particles toward a focal area comprising a well containing a fluid. The well extends out of a plane of the matrix. The method comprises allowing the particles to enter the well and, once in the well, to move within the well out of the plane of the matrix. The fluid containing the particles may be collected from the well.

Another aspect of the invention provides a scodaphoresis method. The method comprises applying a scodaphoresis field to particles in a matrix, the scodaphoresis field causing time averaged motion of the particles toward a focal area. While applying the scodaphoresis field, the method injects the particles into the matrix from a sample chamber by applying a quadrupole injection field to the matrix. The quadrupole injection field extends into the sample chamber.

Another aspect of the invention provides a scodaphoresis method. The method comprises for a first period, applying a first scodaphoresis field to a medium containing first and second particles and for a second period, applying a second scodaphoresis field to the medium. The first scodaphoresis field comprises a first driving field having a time variation at a first frequency and a first mobility-altering field having a first phase relationship to the first driving field. The first scodaphoresis field causes net motion of the first and second particles toward a focus area. The second scodaphoresis field comprises a second driving field having a time variation at a second frequency greater than the first frequency and a second mobility-altering field having a second phase relationship to the second driving field that is different from the first phase relationship. The second scodaphoresis field causes net motion of the second particles away from the focus area.

Another aspect of the invention provides a scodaphoresis method. The method comprises applying a time-varying scodaphoresis field to a matrix containing particles. The scodaphoresis field comprises a cyclically-repeating sequence of segments. The method comprises setting a shape and/or aspect ratio of an area into which the particles are focused by scodaphoresis by changing a relative duration of one or more of the segments relative to others of the segments.

Further aspects of the invention and features of specific embodiments of the invention are described below.

BRIEF DESCRIPTION OF THE DRAWINGS

The accompanying drawings illustrate non-limiting example embodiments of the invention.

DESCRIPTION

Throughout the following description, specific details are set forth in order to provide a more thorough understanding of the invention. However, the invention may be practiced without these particulars. In other instances, well known elements have not been shown or described in detail to avoid unnecessarily obscuring the invention. Accordingly, the specification and drawings are to be regarded in an illustrative, rather than a restrictive, sense.

Figure 1:
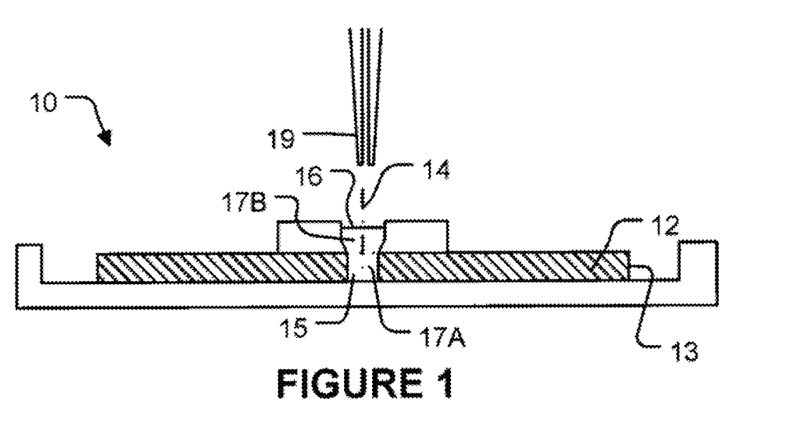
FIG. 1 is a schematic drawing illustrating a cross section of an apparatus for collecting particles from a medium.
Figure 1A:
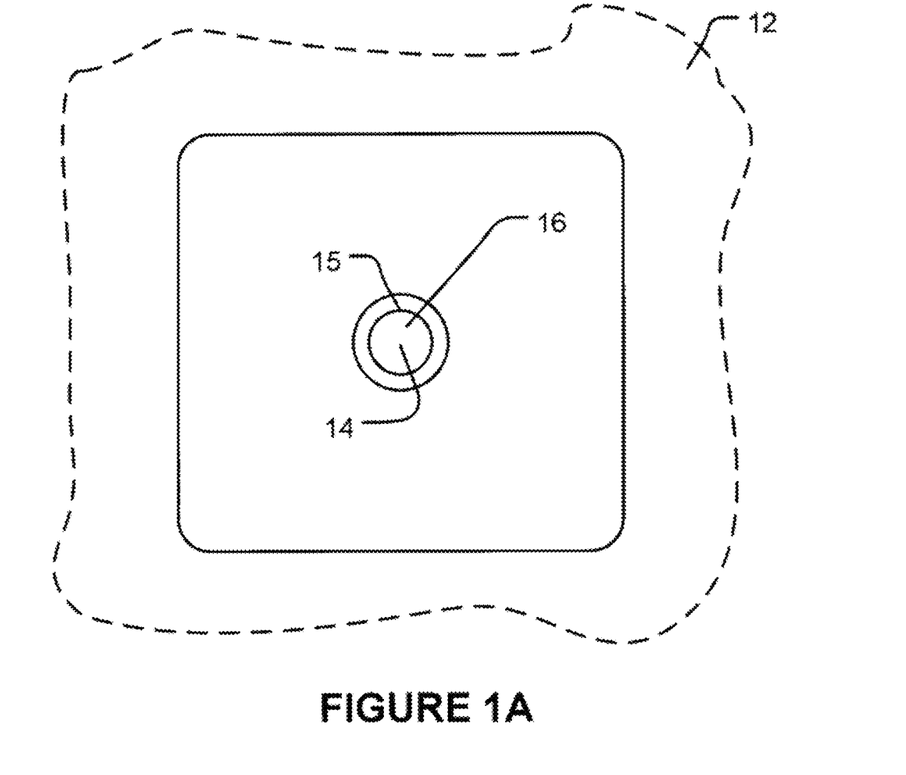
FIG. 1A is a plan view of a matrix portion of apparatus like that shown in FIG. 1.

FIG. 1 illustrates apparatus 10 for collecting particles from a medium 12. In this example embodiment, medium 12 is a medium in which the particles have a non-linear response to a SCODA field. The particles are driven by the SCODA field to move toward a focus location 14. In example embodiments medium 12 comprises a layer of a suitable gel such as an agarose gel or a polyacrylamide gel. In the illustrated embodiment, medium 12 is arranged in a layer 13. A well 15 containing a fluid 16 extends into medium 12 at location 14. Particles in layer 13 that approach location 14 pass into fluid 16 through the edges of medium 12 that bound well 15. Particles can be recovered by removing fluid 16 containing the particles from well 15.

In some embodiments, the mobility of particles in fluid 16 is not field-dependent or is field-dependent to a much smaller degree than it is in medium 12. Consequently, SCODA focussing ceases or becomes substantially reduced when particles enter fluid 16. the concentration of particles in fluid 16 increases as the SCODA field continues to urge particles in medium 12 toward location 14.

Particles can leave fluid 16 by diffusing back into medium 12. The rate at which particles diffuse back into medium 12 is proportional to the concentration of the particles in fluid 16. A maximum concentration of particles in fluid 16 is reached at the point where particles leave fluid 16 by diffusion back into medium 12 at the same rate as particles are brought into fluid 16 from medium 12 by reason of the application of SCODA field(s). This can limit the recovery of particles.

In the apparatus shown in FIG. 1, a more complete transfer of particles into fluid 16 is achieved by providing a well 15 that extends out of the plane of layer 13. In the illustrated embodiment, well 15 has a volume 17A in the plane of layer 13 and a volume 17B that is above the plane of layer 13. Fluid 16 fills both of volumes 17A and 17B. Particles can diffuse from volume 17A into volume 17B thereby reducing the concentration in volume 17A and reducing a rate of diffusion of particles back into layer 13.

A pipetter 19 (only the tip of which is shown in FIG. 1) may be advanced into well 15 and used to withdraw fluid 16 containing particles from well 15.

Figure 2A:
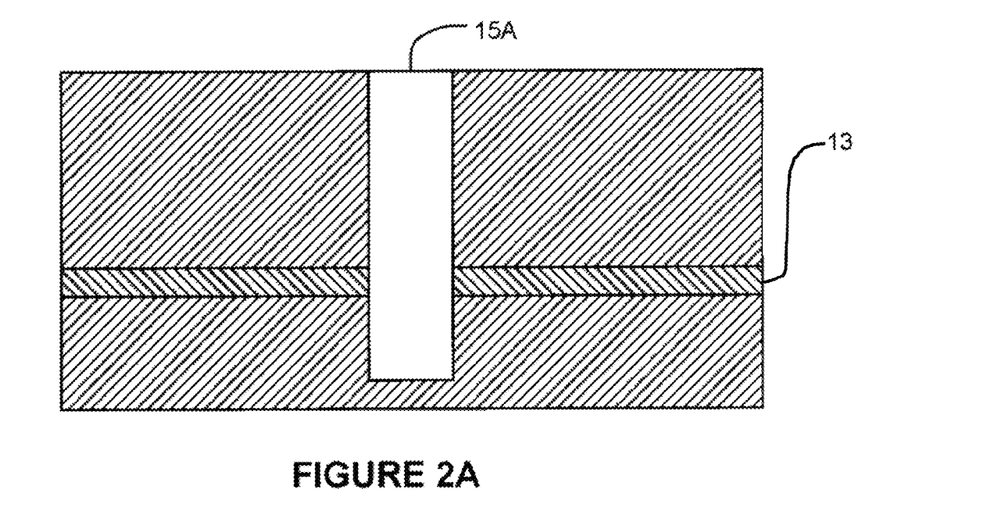
FIGS. 2A through 2F are schematic cross-section views through collection wells according to example embodiments.
Figure 2B:
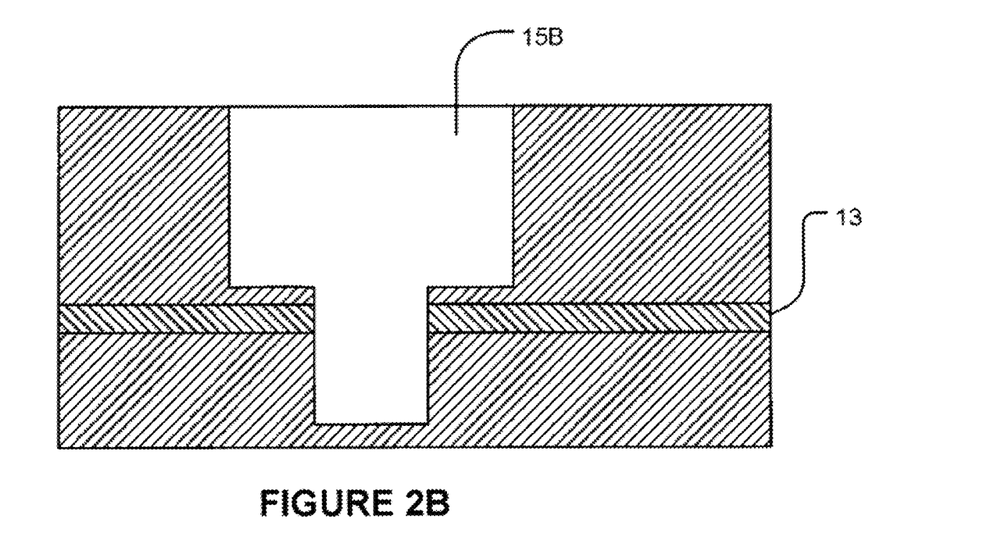
Figure 2C:
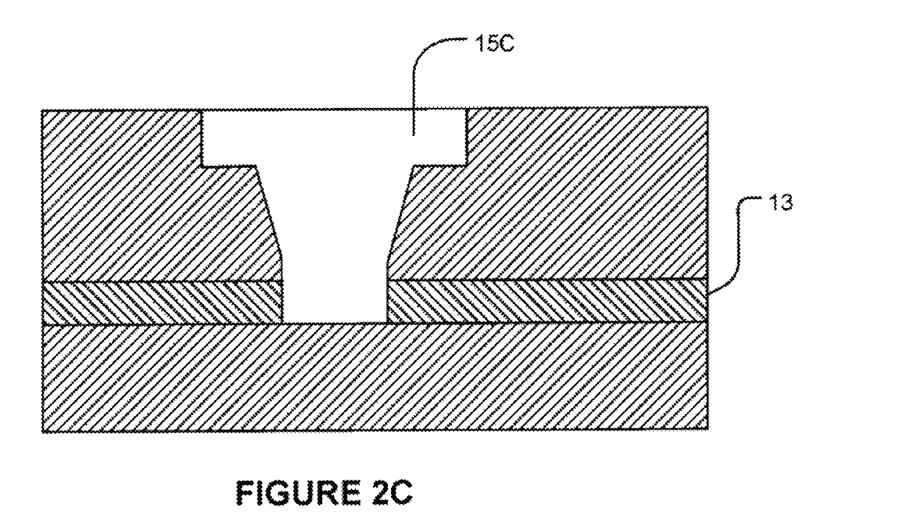
Figure 2D:
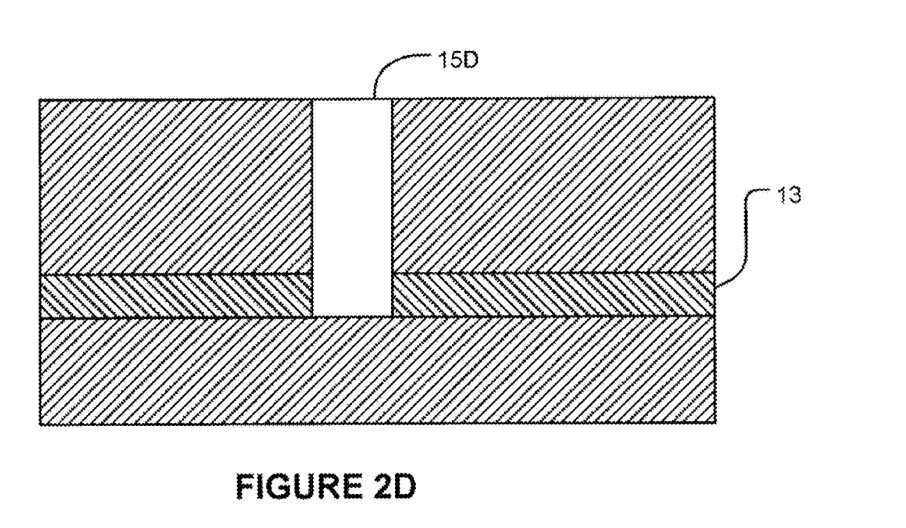
Figure 2E:
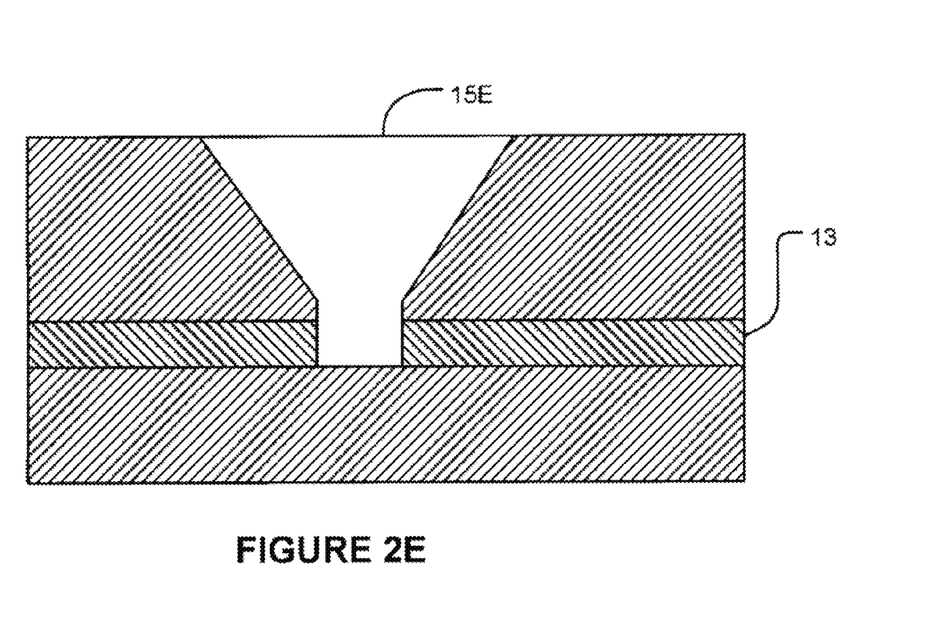
Figure 2F:
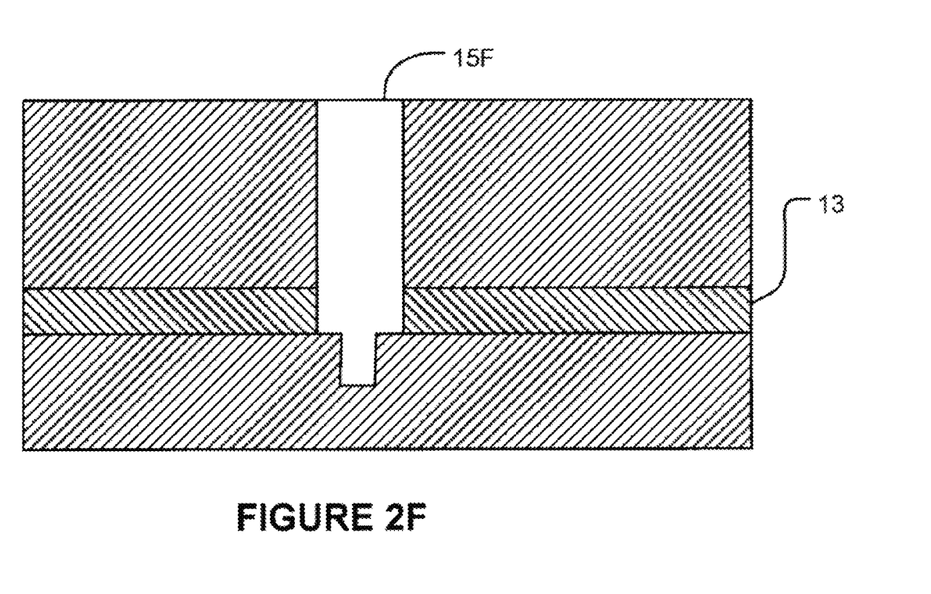

FIGS. 2A through 2E show schematically various possible configurations for wells that include volumes out of a plane of a layer 13. FIG. 2A shows a cylindrical well 15A that extends through layer 13 and has volumes both above and below a plane of layer 13. FIG. 2B shows a well 15B that is smaller in cross section in the plane of layer 13 and larger in cross section above the plane of layer 13. FIG. 2C shows a well 15C that is smaller in cross section in the plane of layer 13 and has portions with greater cross sections above and below the plane of layer 13.

It is convenient but not mandatory that well 15 be circular in cross section. Wells of other cross-sectional shapes (e.g. oval, elliptical, obround, square, triangular, star-shaped, polygonal etc.) could be provided. Advantageously, a diameter of well 15 where well 15 passes through layer 13 is at least equal to a thickness of layer 13. In such embodiments, a ratio of a diameter of well 15 to a thickness of layer 13 is 1:A where A is a positive number with $A \leq 1$.

Figure 3:
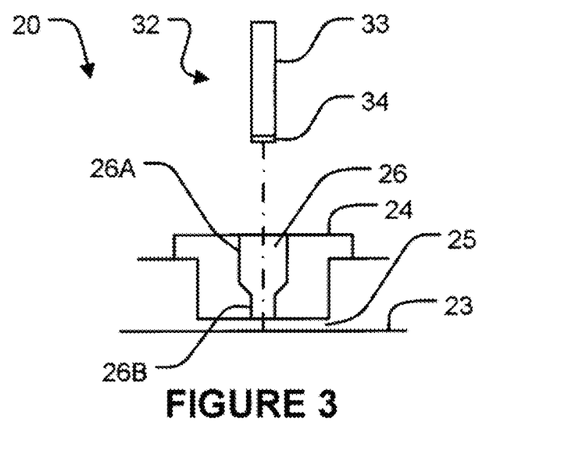
FIGS. 3, 3A and 3B are respectively a partial schematic cross section, a partial exploded view and a schematic plan view showing apparatus according to example embodiments that comprise two-part forms.
Figure 3A:
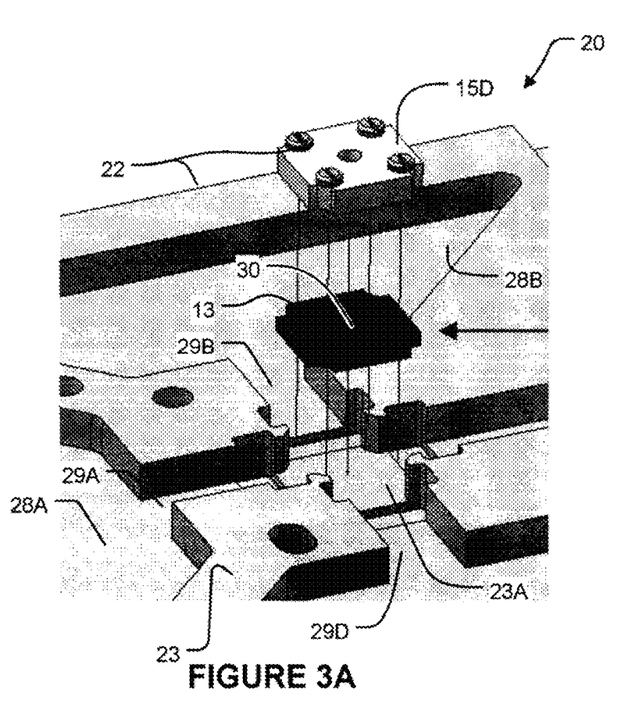
Figure 3B:
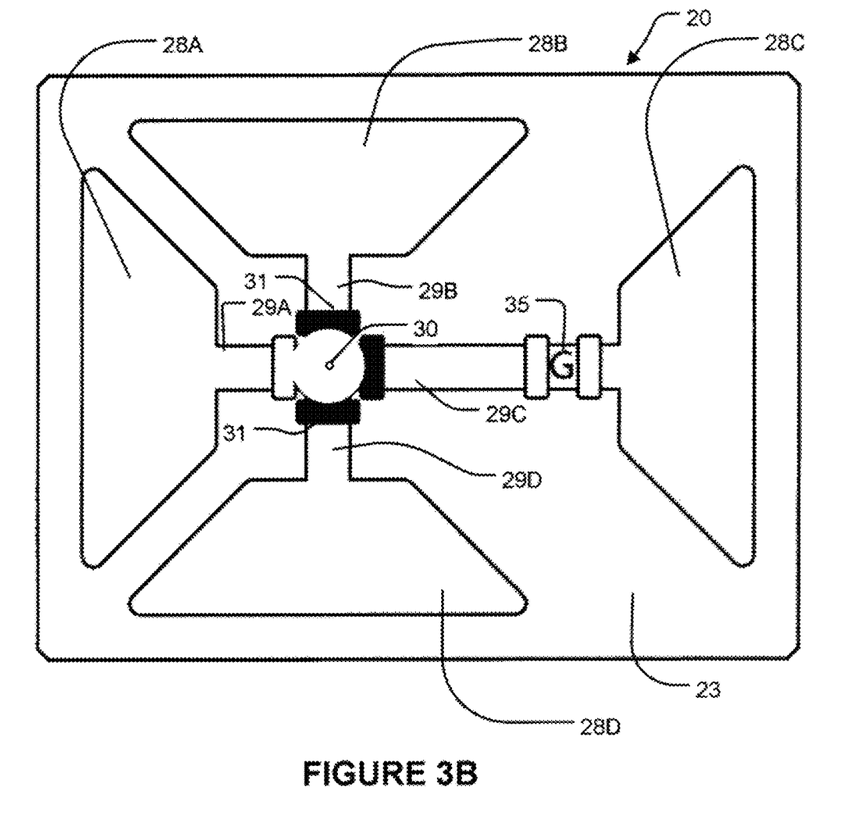

FIGS. 3, 3A and 3B show apparatus 20 comprising two-part forms 22. Form 22 comprises a lower portion 23 and an upper portion 24. Lower portion 23 has a recessed area 23A. Upper portion 24 is arranged to project into recessed area 23A in such a way that a gap 25 having a thickness equal to a desired thickness for layer 13 is defined between upper portion 24 and the bottom of recessed area 23A. Gap 25 has a thickness of 2 mm or less in some example embodiments.

In some embodiments, adjustment mechanisms such as shims, screws, adjustable stops or the like may be provided to permit the thickness of gap 25 to be adjusted. It is not mandatory that lower portion 23 and upper portion 24 be physically separable. In some embodiments, lower portion 23 and upper portion 24 are connected together by hinges or other structure. In some embodiments lower portion 23 and upper portion 24 are parts of a unitary assembly that may be formed, for example, by injection molding.

Form 22 is electrically non-conducting in embodiments in which it is desired to cause particles to move in response to applied electric fields. For example, the components of form 22 may be made from suitable plastics. A prototype was machined from polycarbonate, for example.

A hole 26 passes through upper portion 23 and exits into gap 25. In the illustrated embodiment, hole 26 has a larger-diameter portion 26A and a smaller-diameter portion 26B. In other embodiments hole 26 may have a diameter that does not vary along its length.

In the embodiment shown in FIG. 3B, lower portion 23 comprises chambers 28A, 28B, 28C and 28D that are respectively connected to recessed area 23A by channels 29A, 29B, 29C and 29D (collectively channels 29). A suitable matrix for use in scodaphoresis having a well 30 may be cast in gap 25. This may be done, for example, by inserting a plug 32 (See FIG. 3) through hole 26, pouring a settable matrix material, such as a suitable gel, into gap 25, allowing the matrix material to set, and then removing the plug. Form 22 may be tilted to facilitate filling gap 25 with the matrix material. Removable dams 31 (see FIG. 3B) may be provided in channels 29 to confine the gel to recessed area 23A or another central area.

In an example embodiment, plug 32 comprises a shaft 33 sized and shaped to have a sliding fit in hole 26. A resilient tip 34 is provided on the end of shaft 33. Tip 34 may, for example, comprise polyurethane. Tip 34 can be pressed against lower portion 23 and thereby prevents gel from coming between the end of tip 34 and lower portion 23.

An example embodiment used to make prototype apparatus had the form shown in FIGS. 3A and 3B. Three dams 31 are inserted to block channels 29B, 29C and 29D and plug 32 is inserted through hole 26. The entire assembly is tilted to an angle of approximately 30 degrees to the horizontal. A settable gel is poured into channel 29A until the gel fills gap 25 around plug 32. After the gel sets, plug 32 is removed, dams 31 are removed and any excess gel is removed from channel 29A. A well extending through the resulting layer of gel is provided by hole 26 and the space left in the gel layer after the removal of plug 32.

Some embodiments have one or more optional features. For example, an electrode or electrodes may be provided in or in electrical contact with well 15. An electrode may be connected to a source of electrical potential that maintains the electrode at a potential such that particles of interest are attracted to the electrode. The electrical potential of the electrode may be maintained at a level low enough that the particles of interest are not electrochemically degraded in case they come into contact with the electrode. for example the applied potential may be at a level that is below the electrochemical potential for the electrode(s). In some embodiments an electrode is located in well 15 out of the plane of layer 13, The electrode is maintained at a potential that causes particles that enter well 15 to be drawn toward the electrode into a portion of well 15 that is out of the plane of layer 13.

As another example of an optional feature, a stirrer, pump or other mixing apparatus may be provided to assist in the transfer of particles from parts of well 15 adjacent to layer 13 to parts of well 15 away from layer 13. The mixing apparatus, if present, may operate intermittently or continuously.

Optionally, the fluid in well 15 comprises a material or materials that interact with particles that enter well 15 from layer 13 and, in doing so, reduce diffusion of particles back into layer 13. By way of example, where the particles comprise large molecules, such as DNA, well 15 may contain beads having a coating that has an affinity for DNA such that the DNA cannot easily reenter layer 13 when attached to the beads. As another example, the fluid may contain molecules that tend to cause DNA that enters well 15 to adopt a conformation that makes it difficult for the DNA to re enter layer 13.

In some embodiments, well 15 contains a total volume of fluid that is at least two times larger than a volume of the portion of well 15 that is in contact with layer 13. In some embodiments, well 15 has a depth that is greater than a diameter of the portion of well 15 that passes through layer 13. In some embodiments, well 15 has a size comparable to a size into which particles of interest are focused by SCODA. For example, some applications of SCODA can focus certain particles into spots having diameters on the order of ½ mm in diameter. In some embodiments, well 15 has a diameter of 1 mm to 2 mm or smaller.

In an example of the application of apparatus as described above, particles of interest are introduced into the gel. The particles may be mixed with the gel before the gel is cast into gap 25 or afterward. The particles may be injected into the gel under the influence of an electric field.

In an example embodiment, chambers 28A and 28C were filled with a suitable buffer. The buffer may comprise, for example a 0.25×TBE (Tris-Borate-EDTA) buffer. A sample containing DNA was placed into chamber 35. A potential difference of 90 VDC was applied between electrodes in chambers 28A and 28C. The resulting electrical field caused charged DNA molecules to be driven into the gel over a period of about 90 minutes. Subsequently, chambers 28B and 28D were filled with buffer and SCODA fields were generated by applying suitable potentials to electrodes in the four chambers 28. The SCODA fields caused the DNA molecules to be concentrated into well 15 from where they could be extracted.

New and inventive techniques for injecting particles into a medium is described below. These techniques may be applied in combination with the methods and apparatus described above or in other contexts.

In some embodiments, particles of interest are introduced into a matrix (such as a gel, for example) from two or more sources at the same time. This can be advantageous as it can reduce the time required to introduce particles into a matrix. In some embodiments, a quadrupole electrical field is applied to introduce particles into a matrix from opposed chambers. The quadrupole electrical field and chambers may be symmetrical. A quadrupole field may also be applied to introduce particles into a matrix from a single chamber if desired.

In some embodiments, the quadrupole electrical field is applied simultaneously with SCODA fields such that particles are injected into a matrix by the quadrupole electrical field and simultaneously concentrated and/or separated in the matrix by the SCODA fields. In some such embodiments the SCODA fields comprise time-varying electrical fields that are superposed on the quadrupole field.

Figure 4:
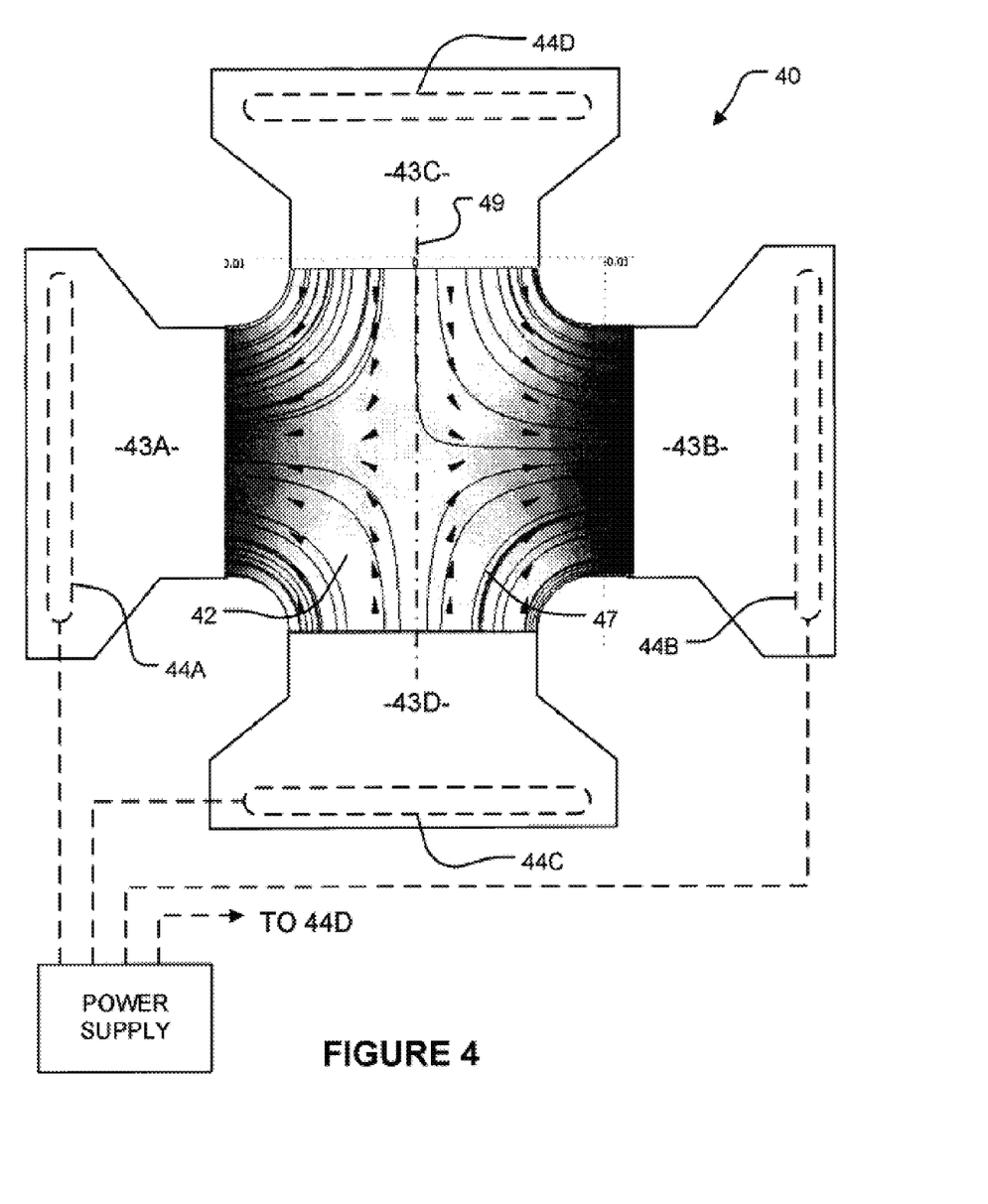
FIG. 4 is a schematic plan view of apparatus comprising a matrix lying between opposed sample chambers.

FIG. 4 is a schematic plan view of apparatus 40 comprising a matrix 42 lying between two opposed chambers 43A and 43B. In the illustrated embodiment, chambers 43A and 43B are mirror images of one another. This is convenient but not mandatory. Electrodes 44A and 44B are in electrical contact with chambers 43A and 43B respectively. Electrodes 44C and 44D are in electrical contact with matrix 42. In the illustrated embodiment, electrodes 44C and 44D make electrical contact with matrix 42 by way of suitable buffer solution in chambers 43C and 43D.

Chambers 43A and 43B contain a fluid or other medium containing particles of interest. The particles respond to electrical fields in such a manner that they tend to be drawn toward one polarity (positive or negative). For example, DNA molecules can tend to have an overall negative charge such that, when placed in an electric field, the DNA molecules will experience a force that tends to move them away from a negative electrode and toward a positive electrode. Other particles of interest may tend to have effective positive charges. A power supply 45 is connected to supply a first potential to electrodes 44A and 44B and a second potential to electrodes 44C and 44D. The result is a quadrupole electrical field. Stream lines 47 indicate the paths that would be taken by positively-charged particles under the influence of the quadrupole injection field. DNA tends to be negatively charged and so DNA would be expected to move in a direction opposite to the arrows shown on stream lines 47. The relative polarity of electrodes 44A and 44B is chosen such that particles of interest tend to be moved into matrix 42 by the resulting electrical field. For example, electrodes 44A and 44B may be maintained at a potential of −X volts relative to some reference voltage while electrodes 44C and 44D are each maintained at a potential of +X volts relative to the reference voltage.

As noted above, a quadrupole field for injecting particles into a matrix may be superposed with a SCODA field, which may also comprise an electric field. In an example embodiment, a SCODA field comprises an electrical field component that rotates at an angular frequency ω and a quadrupole component that varies with time at a frequency 2ω. For example, consider the case where a SCODA field has a component that rotates counterclockwise at an angular frequency ω such that x and y components $E_x$ and $E_y$ are given respectively by:

$$E = E \cos(\omega t) \quad (9)$$

and $$E_y = E \sin(\omega t) \quad (10)$$

and a quadrupole component that varies with time as cos(2ωt). The resulting SCODA field can be approximated by applying predetermined voltages to electrodes 43 for set periods of time. For example, consider the following Table I. Note that $E_x$ in the matrix is at least roughly proportional to the difference between the voltages on electrodes 44A and 44B while E), in the matrix is at least roughly proportional to the difference between the voltages on electrodes 44C and 44D.

TABLE I

Example Voltages for SCODA Field

| Voltage on 44A | Voltage on 44B | Voltage on 44C | Voltage on 44D |
|---|---|---|---|
| +Y − Q | −Y − Q | 0 + Q | 0 + Q |
| 0 + Q | 0 + Q | −Y − Q | +Y − Q |
| −Y − Q | +Y − Q | 0 + Q | 0 + Q |
| 0 + Q | 0 + Q | +Y − Q | −Y − Q |

In Table I, Y is a value giving rise to the rotating component of the SCODA field and Q is a value giving rise to the quadrupole perturbation of the SCODA field.

A constant quadrupole field may be provided by the voltage pattern of Table II, where X is a value giving rise to the quadrupole injection field.

TABLE II

Example Voltages for Quadrupole Field

| Voltage on 44A | Voltage on 44B | Voltage on 44C | Voltage on 44D |
|---|---|---|---|
| −X | −X | +X | +X |
| −X | −X | +X | +X |
| −X | −X | +X | +X |
| −X | −X | +X | +X |

Adding Tables I and II provides a SCODA field (comprising a rotating component and a time-varying quadrupole component) superposed on a static quadrupole injection field as shown in TABLE III.

TABLE III

Example Voltages for Superposed SCODA and Quadrupole Fields

| Voltage on 44A | Voltage on 44B | Voltage on 44C | Voltage on 44D |
|---|---|---|---|
| Y − X − Q (−5 V) | −Y − X − Q (−245 V) | +X + Q (+125 V) | +X + Q (+125 V) |
| −X + Q (+25 V) | −X + Q (+25 V) | −Y + X − Q (−145 V) | +Y + X − Q (+95 V) |
| −Y − X − Q (−245 V) | Y − X − Q (−5 V) | +X + Q (+125 V) | +X + Q (+125 V) |
| −X + Q (+25 V) | −X + Q (+25 V) | +Y + X − Q (+95 V) | −Y + X − Q (−145 V) |

Table III shows in brackets the voltages for the arbitrary example case where X=50V, Y=120V and Q=75V.

A combined SCODA/quadrupole field may be characterized in various ways. Two measures that tend to be useful in practice are the SCODA/Quadrupole ratio and the Quadrupole/Injection ratio. The SCODA/Quadrupole ratio is given by:

$$Y/Q \quad (11)$$

and the Quadrupole Injection ratio is given by:

$$Q/X \quad (12)$$

Combined SCODA/Quadrupole injection may be performed with a wide range of these values.

In some embodiments it is desirable to have a SCODA/Quadrupole ratio in the range of 0.1 to 1 to obtain a small orbit during the SCODA field rotations, and thus a tight focus spot, or in the range of 1.3-3 to optimize for speed. According to certain numerical simulations, 2.1±20% is an optimum SCODA/Quadrupole ratio for highest speed. In some embodiments it is desirable to have the Quadrupole/Injection ratio in the range of 1-3 for samples that are more conductive than the gel or other matrix material, as this will decrease injection time. Quadrupole/Injection ratios in the range of 4-10 may be used in some embodiments where particles of interest have small values of k. Larger quadrupole/injection ratios increase the magnitude of the focusing forces relative to the particle injection forces. With larger quadrupole/injection ratios, particles having relatively small values for k can be transported to the central region by scodaphoresis forces before they are washed off the gel following streamlines of the injection field. The application of the invention is not limited to specific ratios except as may be expressly claimed.

Another example of a combined quadrupole and SCODA field is shown in Table IV.

TABLE IV

Example Voltages for Superposed SCODA and Quadrupole Fields

| Voltage on 44A | Voltage on 44B | Voltage on 44C | Voltage on 44D |
|---|---|---|---|
| 8.04 | −136.72 | 64.34 | 64.34 |
| 42.89 | 42.89 | −115.28 | 29.49 |
| −136.72 | 8.04 | 64.34 | 64.34 |
| 42.89 | 42.89 | 29.49 | −115.28 |

In an example run, the voltages in each row of Table IV were applied respectively for 0.5 seconds, 1 second, 0.5 seconds and 1 second. In the example run the matrix comprised a 16 mm wide slab of 3.5% polyacrylamide gel (29:1 crosslink ratio) prepared with 0.15×TBE buffer. The voltages were cycled between these values for a total run time of 1.5 hours. These voltages correspond to a SCODA/Quadrupole ratio of 1.35:1 and a Quadrupole/Injection ratio of 5.

One advantage of employing a quadrupole injection field with a SCODA field is that it is possible to operate so that contaminant particles being injected tend not to reach a central region of matrix 42 where particles of interest are concentrated by SCODA. SCODA preferentially concentrates particles having high values for k/D. Particles having smaller values for k/D are swept out of the matrix by the quadrupole field before they can be concentrated by the SCODA field into the central region of the matrix. The relative strengths of the SCODA field and the quadrupole field can be adjusted to exclude more particles having smaller values for k/D (by increasing the relative strength of the quadrupole field) or to allow concentration of more particles having smaller values for k/D (by decreasing the relative strength of the quadrupole field).

The presence of a quadrupole field tends to cause any particles concentrated by SCODA to spread out along the axis of the quadrupole field (e.g. along an axis 49 between electrodes 44C and 44D in the illustrated embodiment). This tendency may be counteracted by altering the SCODA fields to provide stronger focusing in the direction parallel to the axis 49. This, in turn, may be done by altering the magnitudes of the SCODA fields and/or by altering the timing of the SCODA fields.

For example, the timing of the SCODA fields may be altered so that proportionally more time is spent in the portions of the cycle wherein the SCODA fields are oriented so as to drive particles in directions generally parallel to the symmetry axis of the quadrupole fields along which the quadrupole field tends to draw particles out of the matrix. Consider the case illustrated in the following Table V which shows electrical potentials for a SCODA field (the quadrupole injection field is not included in Table V).

TABLE V

Example Voltages for SCODA Field

| Voltage on 44A | Voltage on 44B | Voltage on 44C | Voltage on 44D |
|---|---|---|---|
| 42 | −282 | 120 | 120 |
| 120 | 120 | −282 | 42 |
| −282 | 42 | 120 | 120 |
| 120 | 120 | 42 | −282 |

Figure 5A:
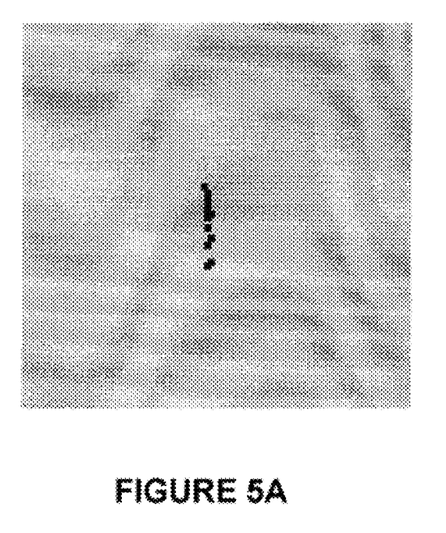
FIGS. 5A and 5B show the results of numerical simulations of the concentration of particles when SCODA fields are applied simultaneously with a quadrupole injection field.

Application of the voltages in the rows of TABLE V for equal time periods (for example 1 second for each row of Table V) on top of a quadrupole field for which electrodes 44C and 44D are an axis of symmetry of the quadrupole field along which the quadrupole field tends to draw particles out of the matrix results in particles being focused into an area that is elongated in the direction between electrodes 44A and 44B as shown in FIG. 5A (which represents results of a numerical simulation).

Figure 5B:
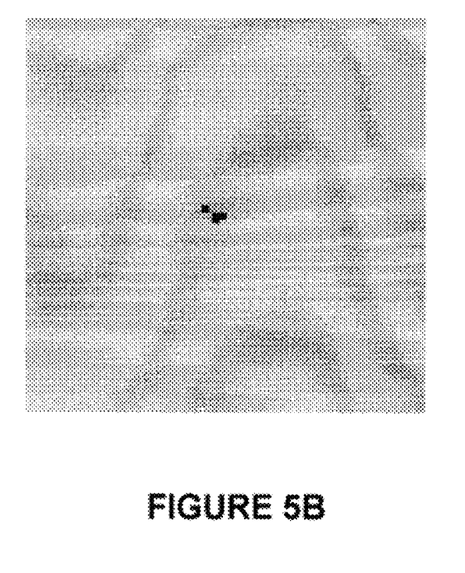

By changing the duty cycle of the applied voltages such that the voltages of the first and third rows of Table V are presented for a shorter time in each cycle (e.g. 1 seconds each) while the voltages of the second and fourth rows of Table V are presented for a relatively longer time in each cycle (e.g. 1.2 seconds each) then the SCODA focusing becomes asymmetrical and the shape of the area into which particles are focused under the combined SCODA and quadrupole fields becomes more symmetrical as shown in FIG. 5B (which represents results of a numerical simulation). This, in turn, permits the application of larger quadrupole fields. The application of larger quadrupole fields both permits more rapid injection of particles into a gel or other matrix and permits sharper selection of particles having higher values of k.

In some embodiments a ratio of a time period during which a SCODA field is applied to generate forces on particles that are oriented parallel to the symmetry axis of the quadrupole field along which the quadrupole field tends to draw particles out of the matrix is 2 times or more longer than the time periods during which the SCODA field is applied to generate forces oriented perpendicular to that symmetry axis of the quadrupole field. For example, numerical simulations have been performed which demonstrate suitable SCODA separation with duty cycle variations for quarter cycles of the SCODA waveform (e.g rows of Table V) of 1, 2.8, 1, and 2.8.

In some embodiments the phase of the perturbing component of the SCODA field (e.g. the phase of the perturbing quadrupole component given by Equations (5) and (6)) is shifted by 180 degrees. This is effectively the same as multiplying equations (5) and (6) by −1. The result is that the average drift velocity imposed on particles in the matrix by the SCODA fields is away from the origin. Such phase shifting may be applied to exclude certain particles from the SCODA focus point.

For example, the field rotation frequency ω may be controlled to selectively focus DNA in certain length ranges. Slower field rotations tend to focus DNA of all lengths (up to the point that the rotations are so slow that diffusion overcomes the SCODA focusing effect). By contrast, more rapid field rotations tend to favor the collection of shorter DNA fragments. Thus, smaller DNA fragments may be preferentially collected by selecting a relatively high frequency for the rotational component of the SCODA field.

Larger DNA fragments may be preferentially collected by shifting the phase of the perturbing component of the SCODA field. For example, to collect longer DNA fragments and exclude shorter DNA fragments at the SCODA focus one may perform SCODA with a frequency low enough to act on the longest DNA of interest with the perturbing component of the SCODA field phased to cause an average movement toward a SCODA focus region. This is continued until DNA has accumulated at the SCODA focus region. Subsequently, one may perform SCODA with a frequency high enough to not act significantly on DNA of interest but low enough to act on shorter DNA fragments with the perturbing component of the SCODA field phased to cause an average movement away from the SCODA focus region. The result is that longer DNA fragments are left behind in the SCODA focus region while smaller DNA fragments are carried out of the SCODA focus region. By appropriately selecting frequencies for the low- and high-frequency phases one can select molecule lengths to be left in the SCODA focus region.

For example, an experiment was conducted in which lambda DNA having a size of 48.5 kb (kilo base-pairs) was separated from puc19 DNA having a size of 2.7 kb. A 1:1 mix of puc19 and lambda DNA was injected into a 1% agarose gel matrix made from 0.25×TBE buffer. Pairs of electrodes were spaced apart by 2.5 cm. Focusing voltages as set out in Table VI were applied. The voltages in each row of Table VI were applied in rotating sequence for 10 seconds each for a total time of 90 minutes. This concentrated both the lambda DNA and puc19 DNA in a SCODA focus region.

Subsequently a higher frequency reverse-phase SCODA field was applied. In the experiment, the reverse-phase SCODA field was applied by using the voltages set out in Table VII with the voltage of each row of Table VII applied in rotating sequence for 1 second for a total of 90 minutes. Analysis of the DNA remaining at the SCODA focus area identified only lambda DNA.

TABLE VI

| First SCODA Field | | | |
|---|---|---|---|
| Voltage on 44A | Voltage on 44B | Voltage on 44C | Voltage on 44D |
| 13.5 | −49.5 | 18 | 18 |
| 18 | 18 | −49.5 | 13.5 |
| −49.5 | 13.5 | 18 | 18 |
| 18 | 18 | 13.5 | −49.5 |

TABLE VII

| Second SCODA Field | | | |
|---|---|---|---|
| Voltage on 44A | Voltage on 44B | Voltage on 44C | Voltage on 44D |
| 49.5 | −13.5 | −18 | −18 |
| −18 | −18 | −13.5 | 49.5 |
| −13.5 | 49.5 | −18 | −18 |
| −18 | −18 | 49.5 | −13.5 |

In methods according to some embodiments, SCODA is performed by applying in alternation a first SCODA field having a lower frequency that produces net motion toward a SCODA focus area and a second SCODA field having a higher frequency that produces a net motion away from the SCODA focus.

Some particles, for example very long DNA can have a mobility that decreases with increasing field within at least some range of field strengths (i.e. the value of k is negative for such particles). The very long DNA may become 'pinned' in a matrix (so that its mobility approaches zero) as field strength increases to high levels. Reverse phase SCODA may be applied in some cases to concentrate such particles. Some SCODA methods concentrate particles by performing reverse phase SCODA using fields having strengths in a range where k is negative for particles of interest. In some such embodiments the particles of interest are long DNA.

Figure 6:
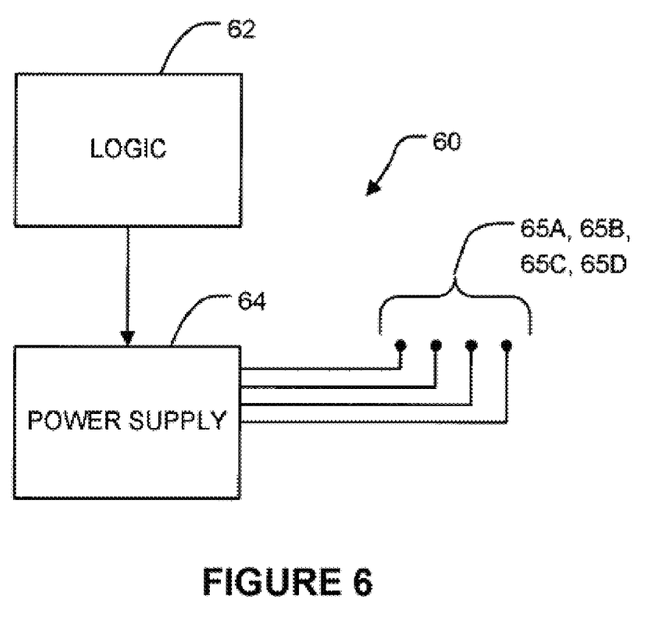
FIG. 6 is a block diagram illustrating a SCODA controller according to an embodiment of the invention.

FIG. 6 shows a SCODA controller 60 according to another example embodiment of the invention. Controller 60 comprises a logic unit 62 which may comprise a data processor executing software instructions, hard-wired logic circuits, a suitably-configured configurable logic device (such as a field-programmable gate array), a suitable combination thereof, or the like. Logic unit 62 controls the operation of a power supply 64 having multiple outputs 65. In the illustrated embodiment, power supply 64 has four independently-controllable outputs 65A to 65D. Other embodiments may provide a different number of outputs. In yet other embodiments one output of power supply 64 is not independently controllable. Outputs 65 may be connected to electrodes associated with a SCODA matrix such as the electrodes of apparatus described above or as described in PCT application WO 2005/072854A1 entitled Scodaphoresis and methods and apparatus for moving and concentrating particles; PCT application WO 2006/081691A1 entitled Apparatus and methods for concentrating and separating particles such as molecules; and Novel electrophoresis mechanism based on synchronous alternating drag perturbation, Marziali, A.; Pel, J.; Bizotto, D.; Whitehead, L. A. Electrophoresis 2005, 26, 82-89, for example.

Logic unit 62 is configured to cause power-supply 64 to apply time-varying voltages to outputs 65 so as to provide one or more of:
  a SCODA field superposed with a quadrupole particle injection field as illustrated, for example, in Table III above.
  a first SCODA field having a first relative phase and frequency suitable for concentrating a type of particles of first and second types of for a first period and then changing over to a second SCODA field having a second relative phase and frequency suitable for deconcentrating particles of the second type for a second period.

In some embodiments, logic 62 comprises a timer and/or a counter and is configured to switch from controlling power supply 64 to apply the first SCODA field to controlling power supply 64 to applying the second SCODA field after the passage of a predetermined time and/or a predetermined number of cycles of the first SCODA field. Parameters defining the first and second SCODA fields may be stored in memory locations, registers and/or control settings accessible to logic 62.

It is not mandatory that outputs 65 be directly connectable to electrodes to provide the SCODA fields. In some embodiments, outputs 65 control devices that provide SCODA fields that consist of or include fields other than electrical fields.

Features of the example embodiments described herein may be combined in further ways to provide additional embodiments.

Where a component (e.g. a gel, matrix, assembly, device, circuit, etc.) is referred to above, unless otherwise indicated, reference to that component (including a reference to a "means") should be interpreted as including as equivalents of that component any component which performs the function of the described component (i.e., that is functionally equivalent), including components which are not structurally equivalent to the disclosed structure which performs the function in the illustrated exemplary embodiments of the invention.

As will be apparent to those skilled in the art in the light of the foregoing disclosure, many alterations and modifications are possible in the practice of this invention without departing from the spirit or scope thereof. For example:

As discussed in the patent applications and paper referred to in the Background section above, SCODA may be performed with a wide range of different field types. SCODA fields may be homogeneous (e.g. SCODA focusing is performed by the application of electrical fields) or heterogeneous (e.g SCODA focusing results from the application of fields of two different types). Methods and apparatus as described herein are not limited to applications in which the SCODA fields are electrical fields or to applications in which the SCODA fields are homogeneous.

Accordingly, the scope of the invention is to be construed in accordance with the substance defined by the following claims.

What is claimed is:

1. Apparatus for collecting particles, the apparatus comprising:
a layer of a matrix material between first and second parts of a form;
a SCODA controller comprising a power supply for supplying electrical potentials to a plurality of electrodes spaced apart around a circumference of the layer of matrix material in order to apply a SCODA field to the matrix material, the SCODA field operable to concentrate particles in the layer into a focus zone; and
a well passing through the layer of matrix material in the focus zone and extending out of the layer of the matrix material into at least the second part of the form.

2. Apparatus according to claim 1 wherein a first portion of the well passing through the layer has a first diameter and a second portion of the well in the second part of the form has a second diameter larger than the first diameter.

3. Apparatus according to claim 1 wherein the first part of the form comprises a recessed area, the second part of the form comprises a projection that projects into the recessed area and the first and second parts are configured to define a gap having a thickness equal to a desired thickness for the layer between the projection and a bottom of the recessed area.

4. Apparatus according to claim 1 wherein the form is electrically non-conducting.

5. Apparatus according to claim 1 comprising a plug that is removably insertable into the well wherein the plug comprises a shaft that is a sliding fit into a hole extending through the second part of the form and a resilient tip on an end of the shaft.

6. Apparatus according to claim 1 comprising a mixer operatively associated with the well, the mixer operable to homogenize fluid in the well.

7. Apparatus according to claim 1 wherein the matrix comprises a gel.

8. Apparatus according to claim 1 comprising beads in the well, the beads having affinity for particles of interest.

9. Apparatus according to claim 8 wherein the beads have affinity for DNA.

10. Apparatus according to claim 1 comprising a plurality of sample injection chambers.

11. Apparatus according to claim 10 wherein the plurality of chambers comprise first and second chambers on opposing sides of the matrix and the apparatus comprises a plurality of electrodes located to apply an electrical quadrupole injection field to the matrix.

12. Apparatus according to claim 11 wherein the plurality of electrodes comprises first and second electrodes located respectively in the first and second chambers and third and fourth electrodes on either side of the matrix and located on a second axis extending at right angles to a first axis extending between the first and second electrodes.

13. Apparatus according to claim 12 wherein the well is located at an intersection of the first and second axes.

14. A scodaphoresis method comprising:
applying a scodaphoresis field to particles in a matrix, the scodaphoresis field causing time averaged motion of the particles toward a focal area comprising a well containing a fluid, the well extending out of a plane of the matrix;
allowing the particles to enter the well and, once in the well, to move within the well out of the plane of the matrix; and
collecting the fluid containing the particles from the well.

15. A method according to claim 14 comprising homogenizing the fluid in the well prior to collecting the fluid.

16. A method according to claim 15 comprising homogenizing the fluid while applying the scodaphoresis field.

17. A method according to claim 14 comprising injecting the particles into the matrix while applying the scodaphoresis field to the particles in the matrix.

18. A method according to claim 17 wherein injecting the particles into the matrix comprises applying a quadrupole injection field to the matrix by way of a plurality of electrodes including an electrode in a sample chamber adjoining the matrix.

19. A method according to claim 18 comprising simultaneously injecting particles into the matrix from a plurality of sample chambers.

20. A method according to claim 19 wherein the plurality of sample chambers are located symmetrically with respect to the quadrupole field.

21. A method according to claim 14 wherein the particles comprise DNA.

22. A method according to claim 14 comprising providing in the well beads having an affinity for the particles and allowing the particles to bond to the beads in the well.

23. A method according to claim 14 comprising changing a conformation of the particles in the well to a conformation wherein the particles are inhibited from diffusing back into the matrix.

* * * * *